United States Patent
Tamura et al.

(10) Patent No.: US 6,869,763 B1
(45) Date of Patent: Mar. 22, 2005

(54) MICROARRAY CHIP AND METHOD FOR INDEXING THE SAME

(75) Inventors: Takuro Tamura, Kanagawa (JP); Kenji Yamamoto, Kanagawa (JP); Toshimasa Watanabe, Kanagawa (JP); Jyunji Yoshii, Kanagawa (JP)

(73) Assignee: Hitachi Software Engineering Co., Ltd., Kanagawa (JP)

( * ) Notice: Subject to any disclaimer, the term of this patent is extended or adjusted under 35 U.S.C. 154(b) by 503 days.

(21) Appl. No.: 09/762,134
(22) PCT Filed: Jun. 1, 2000
(86) PCT No.: PCT/JP00/03554
§ 371 (c)(1), (2), (4) Date: Jan. 31, 2001
(87) PCT Pub. No.: WO00/73504
PCT Pub. Date: Dec. 7, 2000

(30) Foreign Application Priority Data

Jun. 1, 1999 (JP) .............................. 11/153540

(51) Int. Cl.[7] .......................... C12Q 1/68; C12N 11/16; C12M 1/00; G01N 15/06
(52) U.S. Cl. .............................. 435/6; 435/7.1; 435/174; 435/283.1; 435/287.2; 422/68.1; 422/82.05; 702/19
(58) Field of Search .............................. 435/6, 7.1, 174, 435/283.1, 287.2; 422/68.1, 82.05; 702/19

(56) References Cited

U.S. PATENT DOCUMENTS

| | | | | |
|---|---|---|---|---|
| 5,677,195 A | * | 10/1997 | Winkler et al. | 436/518 |
| 5,677,197 A | | 10/1997 | Gordon et al. | |
| 5,763,870 A | * | 6/1998 | Sadler et al. | 250/201.2 |
| 5,812,272 A | | 9/1998 | King et al. | |
| 5,840,485 A | | 11/1998 | Lebl et al. | |
| 6,188,783 B1 | * | 2/2001 | Balaban et al. | 382/129 |
| 6,284,465 B1 | * | 9/2001 | Wolber | 435/6 |
| 6,349,144 B1 | * | 2/2002 | Shams | 382/129 |
| 6,362,004 B1 | * | 3/2002 | Noblett | 436/43 |
| 6,408,308 B1 | * | 6/2002 | Maslyn et al. | 707/104.1 |
| 6,471,916 B1 | * | 10/2002 | Noblett | 422/82.08 |

FOREIGN PATENT DOCUMENTS

| | | |
|---|---|---|
| JP | 11-44647 | 1/1998 |
| WO | WO 97/26539 | 1/1997 |

* cited by examiner

*Primary Examiner*—BJ Forman
(74) *Attorney, Agent, or Firm*—Reed Smith LLP; Stanley P. Fisher, Esq.; Juan Carlos A. Marquez, Esq.

(57) ABSTRACT

A method for indexing and coding element information of at least one biological element provided on a microarray chip thereby identifying the microarray chip. Some of the element spots arranged on the microarray chip are used as index spots to be selectively provided with at a detective colorant. By doing so, the microarray chip is specified, and the element information as well as experimental information of the chip is automatically managed.

5 Claims, 6 Drawing Sheets

Information obtained with Colorant A
(8 × 8 = 64bit)

Information obtained with Colorant B
(8 × 8 = 64bit)

MICROARRAY CHIP AND METHOD FOR INDEXING THE SAME

TECHNICAL FIELD

The present invention relates to a microarray chip having a plurality of biopolymer spots arranged thereon such as DNAs or the like that specifically hybridize with particular DNAs or proteins, and to a method for indexing the microarray chip for identification.

BACKGROUND ART

In the field of molecular biology, microarray chips, as represented by a biochip on which biopolymers such as DNAs or proteins are high-densely immobilized, have lately and rapidly become of interest. For an experiment using the microarray chip, numbers of supports (chips) with diverse types of elements (probes) immobilized thereon are produced. The elements on each chip are subjected to reaction with a sample (target) of a test subject. The difference of the reaction between the elements and the sample on one chip may be detected by a single experiment. The difference of the reaction between the same element collections on a plurality of chips may be detected by repeating experiments under different conditions.

In an experiment using a microarray chip, it is necessary to manage the information of diverse types of elements immobilized on the chip. The following methods are practically used for preparing a microarray chip: a method in which elements prepared in wells are immobilized on a support such as a glass slide by using a spotter (arrayer); and a method in which elements are synthesized on a support according to a semiconductor producing technique. In both methods, element information (i.e., which element is to be immobilized on which location on the chip) is prepared as data for preparing the microarray chip.

In an experiment using a microarray chip, the results of the experiment are obtained by detecting color development of part of the element collection immobilized on the chip. In detecting the color development, "the color intensities of the elements" are recorded based on the element information obtained for preparing the microarray chip. Then, the difference of color development between the elements and the difference of color development between the element collections on the chips are analyzed.

Figure 7:
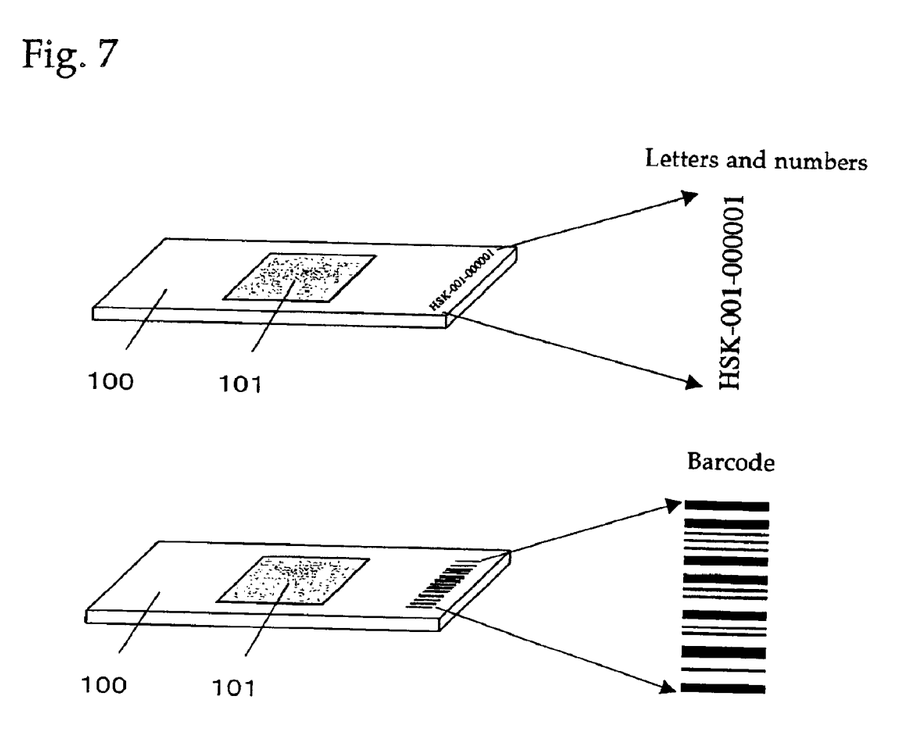
FIG. 7 is a view for illustrating a conventional microarray index.

Since the shapes of the microarray chips are all identical, each individual microarray chip cannot be identified by its appearance, nor can the types of the DNAs immobilized on the chip be identified. As shown in FIG. 7, a method is suggested in which letters, numbers or symbols are printed or barcodes are provided as an index outside a element region 101 on a microarray chip 100 so as to specify the element information to be used for the microarray chip 100.

In specifying the element information to be used for each microarray chip by the method of printing letters, numbers, symbols or barcodes outside the element region of the chip, a mechanism for printing (or sticking) letters, numbers, symbols or barcodes on a chip is required. In addition, in using the microarray chip, mechanisms (or an interface that allows input by an operator) are also required for reading the letter, barcode or the like printed on the chip and for informing the same to an information processing system. As a result, cost of devices such as a letter or barcode reader, input error in case of manual input and the like have been the problems.

Regarding the above-described problems of conventional technique, the present invention aims at providing a microarray chip for which element information to be used can be specified without using letters, barcodes of the like. The present invention also aims at providing a method for indexing a microarray chip for specifying element information to be used for the microarray chip without requiring a special-purpose device for reading the element information such as a letter or barcode reader. The present invention further aims at providing a method for indexing a microarray chip, which enables automatic management of information of the elements on the microarray chip and use of experiment information.

According to the present invention, the above-described aims are accomplished by using some of the spots (element spots) arranged on the microchip array as an index (a microarray index) for managing the element information. According to the present invention, elements themselves are used as an index so that the index can be obtained together with the element information upon reading the microarray chip. Thus, there is no need of preparing a special device for reading the index.

Accordingly, a microarray chip of the invention is characterized by comprising a plurality of spots arranged in a predetermined positional relationship, wherein some of the plurality of spots provide index information for specifying the microarray chip.

The microarray chip of the invention is also characterized by comprising a plurality of element spots arranged in a predetermined positional relationship, wherein spots which provide index information for specifying the microarray chip are positioned along with the element spots.

The spots constructing the microarray index are preferably added with visible colorant beforehand to confirm the index before the experiment, to align the element region and the index region, and to confirm the chip reading direction.

When the microarray chip is prepared by immobilizing elements prepared in wells on a support such as a glass slide by using a spotter (arrayer), elements already bound with a luminescent substance or elements as index spots which allow accumulation of a luminescent substance on the element spots upon the microarray chip experiment are immobilized with the spotter. When the microarray chip is prepared by synthesizing elements on a support according to a semiconductor producing technique, elements which allow accumulation of a luminescent substance on the element spots upon the microarray chip experiment are synthesized on the support.

As described above, the spots used for constructing the index information include spots containing and spots not containing detective colorant, which the index information is based on the presence and absence of the detective colorant. The detective colorant which is used as a fluorescent label for hybridization reaction may be contained in the index spots prior to hybridization reaction, or may be contained in the target and be provided to the spots as a result of the hybridization reaction. The elements to be immbolized as a microarray index may be labeled with a detective colorant beforehand so as to allow the use of the microarray chip index before the experiment of reacting with the target.

In reading the microarray chip image with a microarray chip reader, the index information on the microarray chip are read simultaneously with the element information. By providing a microarray index at a predetermined position, the microarray index may be obtained from the readout image of the microarray chip after the reaction.

A method for indexing the microarray chip according to the present invention is a method for indexing a microarray chip comprising a plurality of spots arranged in a predetermined positional relationship, wherein some of the plurality of spots are used for maintaining index information.

A method for indexing the microarray chip according to the present invention is further a method for indexing a microarray chip comprising a plurality of spots arranged in a predetermined positional relationship, wherein some of the plurality of spots are used as index spots for maintaining index information, and the index information is reproduced by detecting the presence or absence of a detective colorant on the index spots.

In an experiment using a microarray chip where elements which allow accumulation of a luminescent substance on the element spots are immobilized or synthesized on a support, colored ('on') spots for constructing the microarray index are obtained by immobilizing or synthesizing, on a support, a substance that reacts with a substance labeled with a colorant which is present in a sample during the course of the experiment, or a substance that reacts with a substance labeled with a colorant added to the sample. Thus, spot detection is ensured.

Moreover, spot detection error can be avoided by providing parity spots. For example, information detected at the index spots is realigned into a two-dimensional matrix upon reproducing the index information, and part of the spot information of the realigned two-dimensional matrix is used as parity information. If necessary, microarray index may be duplicated by providing them at two positions in the element region, thereby avoiding spot detection error.

Database which uses the microarray as an index may be constructed for storing microarray chip information (preparation date, on-chip-spot location information, conditions of the experiment, etc.) and on-chip-element information (element index, experiment measurement information, etc.). The database also stores element information (index for referring to a public database, gene name, definition of the functions, DNA sequence, etc.) and links with information of the element on chip via the element index. By linking the actual microarray chip and the information in the database via the microarray index obtained from the microarray chip readout image, measurement information can automatically be input into the database.

Specifically, a database is constructed for storing a element information record, a microarray chip master record and an on-chip-element information record. Information of a element is recorded on the element information record where a element index is used as a master index. Information of the microarray chip is recorded on the microarray chip master record where the microarray index is used as a master record. The microarray index, a location of a spot on the microarray chip, element index of the element spotted on that location, and the information of measurement of the spot are recorded on the on-chip-element information record. The microarray chip is linked with the microarray chip master record via the microarray index maintained by the index spots, as well as to the on-chip-element information record. The on-chip-element information record is linked with the element information record via the element index.

BEST MODE FOR CARRYING OUT THE INVENTION

Hereinafter, embodiments for carrying out the present invention will be described with reference to the drawings.

Figure 1A:
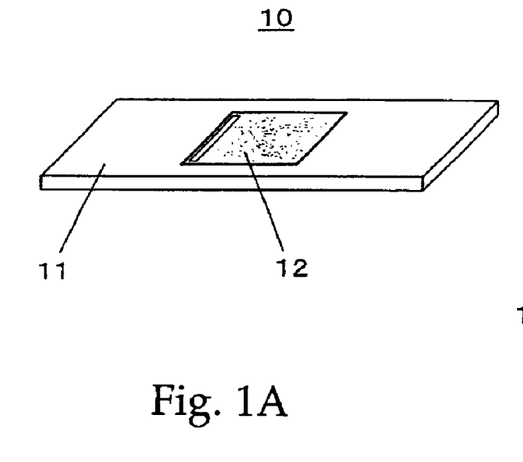
FIGS. 1A and 1B are schematic views showing an exemplary microarray chip of the present invention.
Figure 1B:
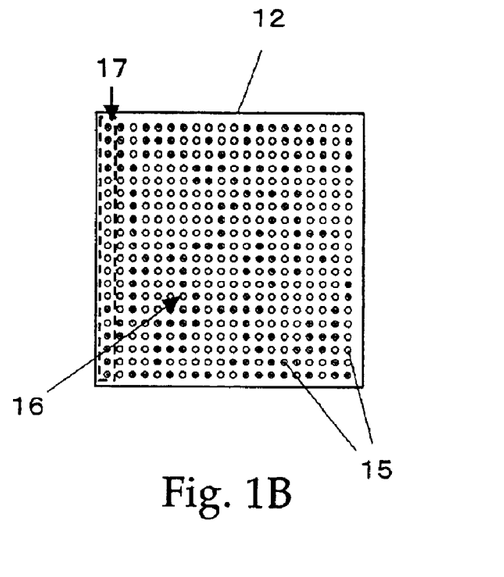

FIGS. 1A and 1B are schematic views showing an exemplary microarray chip provided with a microarray index of the invention. As shown in FIG. 1A, the microarray chip 10 includes a support (chip) 11 such as a glass slide, or a nylon or nitrocellulose membrane, and a element region 12 provided on the support 11. As shown in FIG. 1B, the element region 12 is provided with a microarray 16 in which element spots 15 are high-densely arranged in a two-dimensional array formation by depositing biopolymers such as DNAs or proteins prepared in wells (not shown) on the chip 11 using a spotter (arrayer). Some of the element spots 15 arranged in a two-dimensional array formation to construct the microarray 16 are used as a microarray index 17 as will be described below.

Figure 2:
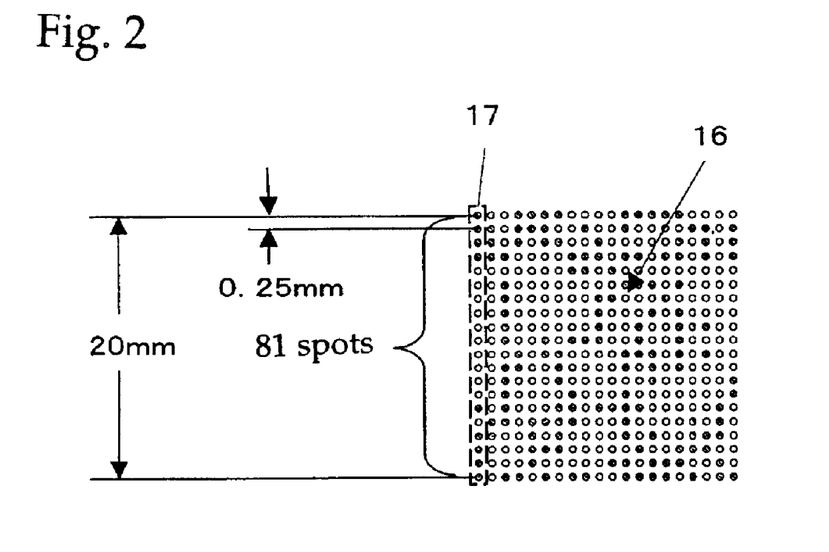
FIG. 2 is a view showing an exemplary microarray provided with a microarray index.

FIG. 2 is a view showing an example of the microarray 16 provided with a microarray index 17 which has an information content of 128 bits according to the present invention. According to this example, four spots are provided per millimeter. One vertical column of the microarray 16 (which consists of 81×81 spots arranged within a 20 mm square element region 12) is used as the microarray index 17. Thus, 81 spots are available as an index, and each spot may or may not be immobilized with a color developing colorant or with a element which enables to accumulate a color developing colorant upon the microarray chip experiment, thereby obtaining 81-bit ON/OFF information. If two color developing colorants (e.g., Cy3 and Cy5) are used for the color development of the elements, each color component can make use of 81 spots since the developed color components from the two co-existing luminescent colorants may separately be detected with a microarray chip reader. According to this method, information of 81×2=162 bits may be used as an index.

Figure 3A:
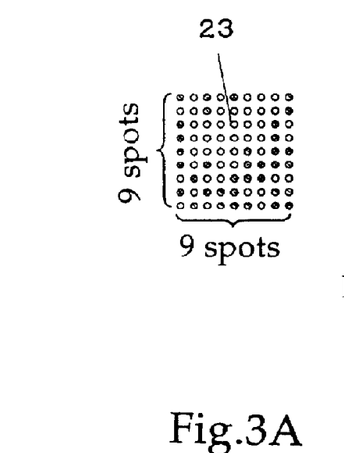
FIGS. 3A to 3C are views for illustrating an exemplary relationship between the index spots in the microarray and index information.

FIGS. 3A to 3C are views for illustrating an exemplary relationship between the 81 index spots in the microarray 16 shown in FIG. 2 and the index information. According to this example, 81 index spots are rearranged into a 9×9 grid 23 as shown in FIG. 3A in order to efficiently provide parity for detecting any error of any spot at a particular position. Spots in a vertical column at the very right and a horizontal row at the very bottom of the rearranged 9×9 grid are used as parity spots 27. The rest of the spots 26 are used for index information and thus the index spots 26 are made up of 8×8=64 spots.

Figure 3B:
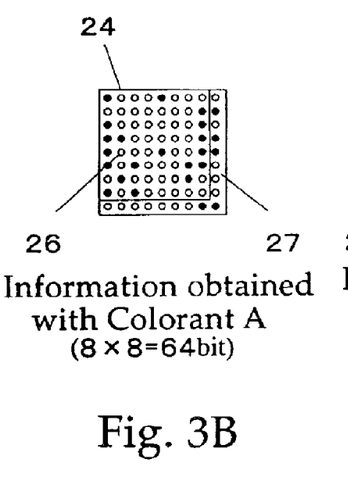
Figure 3C:
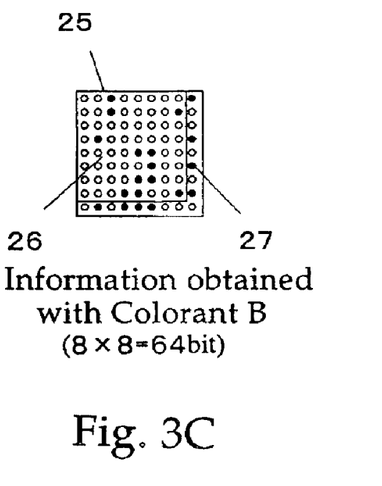

Each spot is provided with two pieces of information with the two types of luminescent colorants A and B. The colorant A gives information 24 of 8×8=64 spots (64 bits) as shown in FIG. 3B, and the colorant B gives information 25 of 8×8=64 spots (64 bits) as shown in FIG. 3C. The parity is set for each piece of information with each colorant and for each column and row of the index spots 26 such that, for example, it is ON if the number of ON spots is an odd number and OFF if an even number. The spot at the right bottom corner is ON if the number of ON spots in the whole index area is an odd number and OFF if an even number. According to this method, highly reliable 64 bit index can be obtained, and 128 bit index can be obtained by using two luminescent colorants.

Figure 4A:
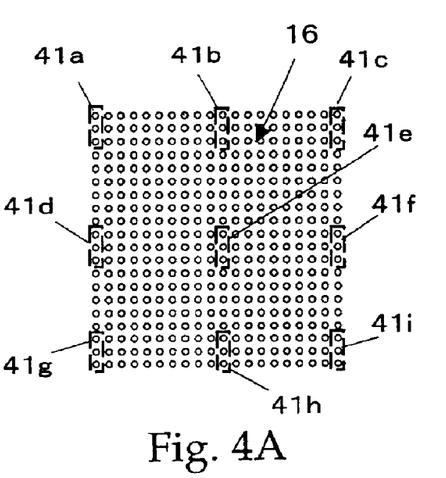
FIGS. 4A to 4D are views for illustrating other exemplary arrangements of the index spots.
Figure 4B:
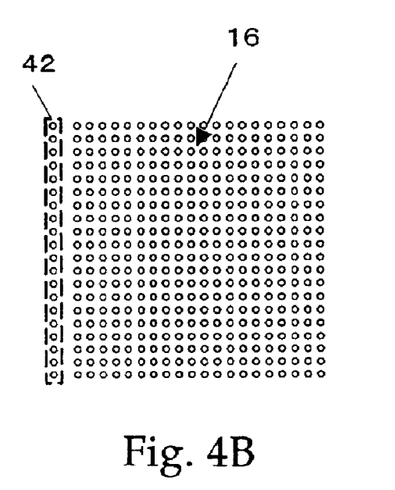

FIGS. 4A to 4D are views for illustrating other exemplary arrangements of the index spots. Referring to FIG. 4A, index spots are dispersively located in the microarray 16. In this example, the index spots are divided into 9 spot groups 41a to 41i and dispersively located at known locations in the microarray 16. The spot groups 41a to 41i in the microarray 16 do not need to be located in a systematic pattern as long as their locations are known. These spot groups are used as index information by rearranging them as shown in FIG. 3A. Referring to FIG. 4B, an index spot column 42 is provided outside the microarray 16 made of the element spots. The index spot column 42 is not limited to a single column and multiple may be formed. The index spot columns may also be provided on both sides of the microarray 16.

Figure 4C:
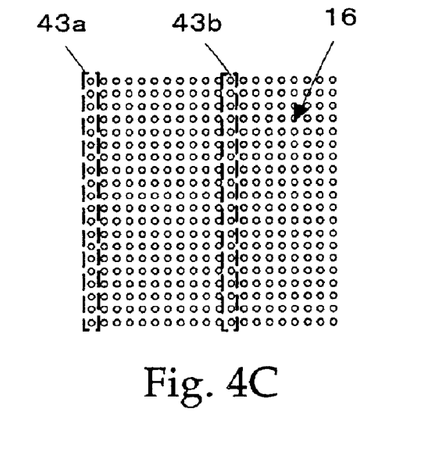
Figure 4D:
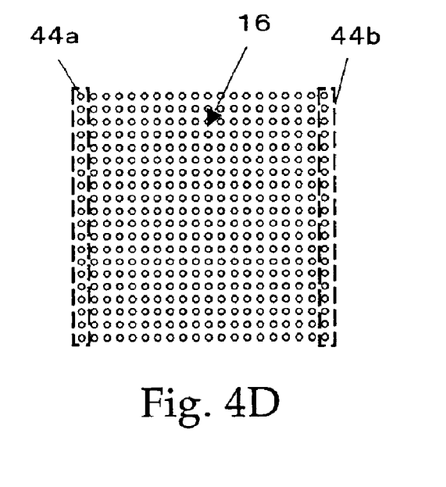

FIG. 4C shows an example where two index spot columns are provided. An index spot column 43a provided on left of the microarray 16 and an index spot column 43b provided at the middle of the microarray 16 may form one index together, or the two spot columns 43a and 43b may carry the same information so that one can be used for verification. FIG. 4D shows an example where two index spot columns 44a and 44b having the same functions as those described with reference to FIG. 4C are provided at both sides of the microarray 16.

Figure 5A:
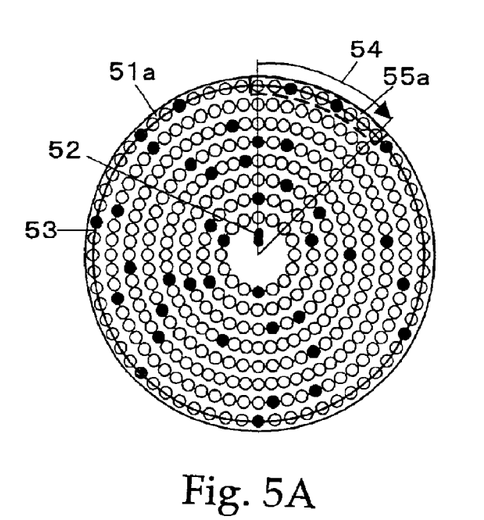
FIGS. 5A to 5C are views for illustrating other exemplary arrangements of the index spots.
Figure 5B:
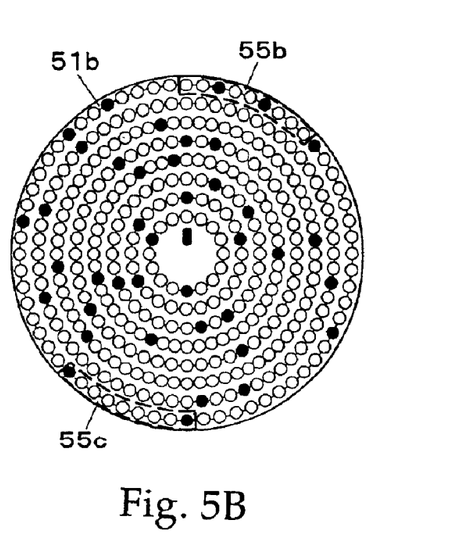
Figure 5C:
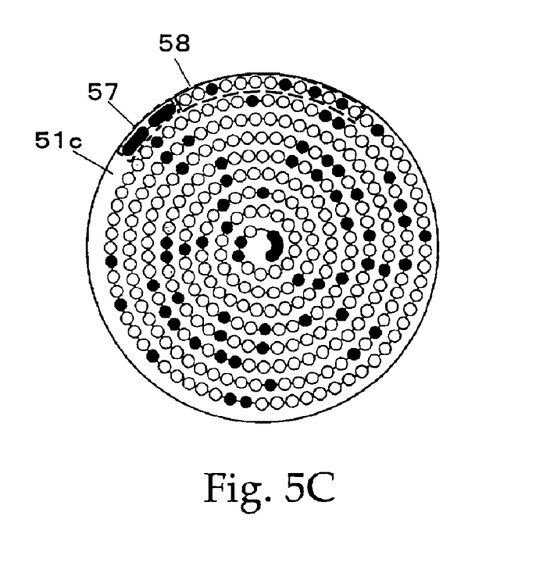

FIGS. 5A to 5C are views for further illustrating other exemplary arrangements of the index spots. In examples shown in FIGS. 5A and 5B, element spots are positioned to form concentric circles on a circular microarray chip. As a whole, the microarray forms a circle. Each element spot on the microarray can be specified with a record 53 which is determined by a distance from the center (radius) of the microarray and a rotation angle 54 determined based on a marker 52 which determines the starting position of the rotation. Some of the spots in the microarray can be used as index spots. FIG. 5A shows an example where sequential spots 55a at the outermost record (record 0) of the microarray 51a and between the rotation angles of 0° and 45° are used as the index spots. FIG. 5B shows an example where sequential spots 55b and 55c at the outermost record 0 and between the rotation angles of 0° and 45° and between 90° and 135°, respectively, are used as the index spots.

According to the example shown in FIG. 5C, each element spot are arranged at equal intervals in a vortex pattern starting from the marker 57 which determines the starting position of the vortex. As a whole, the microarray 51c forms a circle. Each element spot on the microarray 51c can be specified by a distance from the marker 57. Some of the spots on the microarray can be used as index spots. FIG. 5C shows an example where a plurality of element spots 58 following immediately after the marker 57 for determining the starting position of the vortex are used as index spots.

Figure 6:
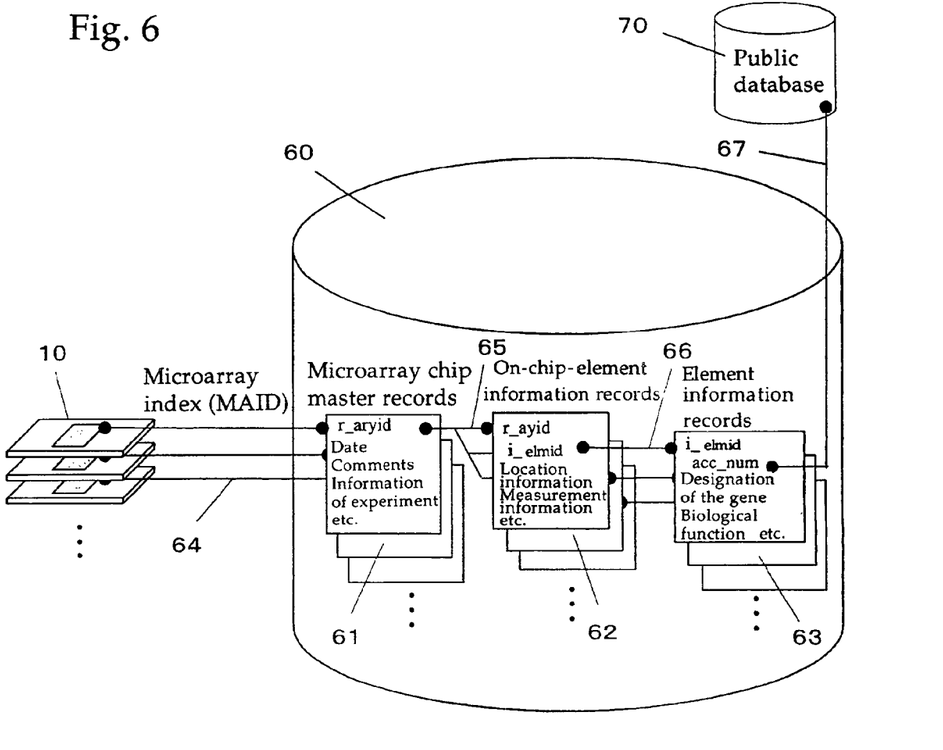
FIG. 6 is a diagram for illustrating links between microarray chips and information in database via microarray indices.

FIG. 6 is a diagram for illustrating links between microarray chips and information in database via a microarray indices. In a microarray chip information database 60, element information that can be used for preparing microarray chips is stored as element information records 63 where element indices (i_elmid) are used as master indices. The element information record 63 stores, according to the type of the element, an index (acc_num) for referring to a public database containing the information of the elements, designations of the gene/protein, biological functions and gene/amino acid sequence as element information.

In preparing the microarray chip 10, a microarray index (with a unique value of, for example, 128 bits) is issued, and microarray chip master records 61 which use the microarray indices (r_aryid) as master indices are added to the microarray chip information database 60. The microarray chip master records 61 store information of the microarray chip to be prepared (date of preparation, comments, etc.) and is provided with a field for storing, for example, conditions of a microarray chip experiment. Furthermore, on-chip-element information records 62 are generated for the same number as that of the elements to be immobilized on the microarray chip and are linked via the same microarray index (65). Each of the on-chip-element information records 62, stores a location of one element on the microarray chip, and stores a element index to be linked (66) to the element information record. A field for storing later-obtained information of a microarray chip experiment and the like is also provided for each element on the microarray chip.

The results of the microarray chip experiment obtained by a microarray chip reader, together with the microarray index prepared on the microarray chip, can automatically be stored in the microarray chip master record 61 specified by the link via the microarray index (64) and in the on-chip-element information record 62 linked with the microarray chip master record.

When the results of the experiment is to be referred in the database 60, detailed information of the element can be obtained from the element information record 63 which links with the on-chip-element information record 65. Since the element information record 63 is independent from the microarray index, it may be shared with a plurality of microarray chip master record 61. Further information can be obtained from the public database 70 by linking (67) to the public database via the index for the public database reference stored in the element information record 63.

INDUSTRIAL APPLICABILITY

According to the present invention, information used for microarray chip application can be automatically managed. Without requiring the user of the microarray chip for a special instrument, a microarray index allows link between information of the microarray experiment and information prepared upon making the microarray chip.

What is claimed is:

1. A method for indexing a microarray chip with a plurality of spots arranged in a predetermined positional relationship thereon, comprising:

selecting some of the plurality of spots as index spots;

spotting at least one biological element onto one of remaining spots as a non-index spot;

indexing the microarray chip spotted with said biological element by selectively providing at least one kind of detective colorant onto the index spots thereby coding in the index spots a unique microarray index value, said microarray index value being linked to element information which includes a type of said biological element and a location of said non-index spot on the chip; and automatedly identifying the microarray chip by detecting said detective colorant provided on said index spots.

2. A method for indexing a microarray chip with a plurality of spots arranged in a predetermined positional relationship thereon, comprising:

selecting some of the plurality of spots as index spots;

spotting at least one biological element onto one of remaining spots as a non-index spot;

indexing the microarray chip spotted with said biological element by selectively providing at least one kind of detective colorant onto the index spots thereby coding in the index spots a unique microarray index value, said microarray index value being linked to element information which includes a type of said biological element and a location of said non-index spot on the chip; and reproducing the element information by detecting the presence or absence of said detective colorant provided on the index spots thereby automatedly identifying the microarray chip.

3. A method of indexing a microarray chip according to claim 2, wherein the index spots are arranged in a two-dimensional matrix including some of the index spots designated as parity spots and provided with said detective colorant based upon a parity algorithm running by row and by column of the matrix, and upon reproducing the element information, the parity spots are checked for errors.

4. A method for indexing a microarray chip according to claim 1, further comprising the steps of:

constructing a database for storing an element information record, a microarray chip master record, and a biological element information record;

recording information of said biological element on the element information record with an element index;

recording information of the microarray chip on the microarray chip master record with a microarray index;

recording, on the biological element information record, information of the microarray index, said location of said non-index spot on the microarray chip, said element index of said biological element spotted on said location, and information of experiment conducted and measurement taken in said non-index spot;

linking the microarray chip with the microarray chip master record as well as the biological element information record via the microarray index coded in the index spots; and linking the biological element information record with the element information record via the element index.

5. A method of indexing a microarray chip according to claim 1, wherein some of the index spots are designated as parity spots and provided with said detective colorant based upon a parity algorithm, and upon reproducing the element information, the parity spots are checked for errors.

* * * * *